(12) United States Patent
Veselinovic

(10) Patent No.: US 8,689,794 B2
(45) Date of Patent: Apr. 8, 2014

(54) DENTAL SHIELD DEVICE

(76) Inventor: Zeljko Veselinovic, LaSalle (CA)

( * ) Notice: Subject to any disclaimer, the term of this patent is extended or adjusted under 35 U.S.C. 154(b) by 465 days.

(21) Appl. No.: 12/663,374

(22) PCT Filed: Feb. 11, 2009

(86) PCT No.: PCT/CA2009/000159
§ 371 (c)(1),
(2), (4) Date: Dec. 7, 2009

(87) PCT Pub. No.: WO2009/100525
PCT Pub. Date: Aug. 20, 2009

(65) Prior Publication Data
US 2010/0163058 A1 Jul. 1, 2010

(30) Foreign Application Priority Data
Feb. 12, 2008 (CA) ..................................... 2621524

(51) Int. Cl.
*A61C 5/14* (2006.01)
*A61C 3/00* (2006.01)
(52) U.S. Cl.
USPC ............................... 128/861; 433/6; 128/859

(58) Field of Classification Search
USPC ................. 128/862, 859, 857, 848, 846, 860, 128/200.26; 433/6, 215, 45, 41, 47, 216; 446/27, 120, 121; 119/821; D24/110.5
See application file for complete search history.

(56) References Cited

U.S. PATENT DOCUMENTS

| 5,427,117 A * | 6/1995 | Thornton ...................... 128/848 |
| 5,957,689 A | 9/1999 | Wagner |
| 6,675,808 B2 | 1/2004 | Karasic |
| 2006/0166163 A1* | 7/2006 | Ye .................................. 433/45 |

FOREIGN PATENT DOCUMENTS

WO 9003199 A1 4/1990

* cited by examiner

*Primary Examiner* — Victoria J Hicks
(74) *Attorney, Agent, or Firm* — McMillan LLP

(57) ABSTRACT

A dental shield for use during intubation to protect teeth, including a plurality of tooth segments, each segment having a male connector and a female connector located on opposite sides for the purpose of attaching each segment to an adjacent segment, and each segment formed from a rigid material defining a tooth-shaped channel containing a deformable material bound to the tooth surface such that a number of tooth segments are assemblable into the dental shield device.

6 Claims, 5 Drawing Sheets

DENTAL SHIELD DEVICE

FIELD OF THE INVENTION

The present invention relates to the field of dental devices. In particular, it relates to a dental device for protecting teeth during intubation of a patient.

BACKGROUND OF THE INVENTION

Patients who are preparing to undergo surgery requiring general anesthetic can find themselves at risk of tooth and dental damage as a result of the oral or nasal intubation process required for the procedure. In order to properly intubate the patient, the mandible and/or maxilla must be leveraged open to permit the laryngoscope blade to be inserted and the airway cleared for intubation. Unfortunately, the leverage required can lead to chipping, cracking, breaking, loss of teeth or possible aspiration of teeth or any fixed or removable dental work if pressure is applied to the teeth in an uneven or excessive manner.

There have been previous attempts to develop dental devices to address this issue. U.S. Pat. No. 3,513,838 to Foderick et al. ("Foderick") discloses a tooth protector, which consists of two plates, an upper and a lower, which are inserted into the mouth to prevent shifting of the intubation tube. The Foderick plates provide a measure of protection to the teeth after intubation, but do not alleviate or address the issue of tooth damage during the insertion phase.

Another attempt is disclosed in U.S. Pat. Nos. 6,623,425 and 7,044,910 to Cartledge et al. ("Cartledge"). Cartledge discloses a modified laryngoscope blade having a detachable insert located above the blade to attempt to reduce the pressure and force associated with the use of the blade for intubation.

Ideally, such a device should be adaptable for use in emergency intubation situations, to reduce the risk of complications arising from the aspiration or ingestion of tooth fragments and other particles that result from tooth damage potentially caused when using existing methods and devices. Potential damage to teeth includes but is not limited to the following: avulsion or loss of teeth, complete fractures of teeth, partial fractures of teeth, loss of fixed prostheses (including crowns, bridges, veneers), loss of removable prosthesis (including unilateral, partial, or complete dentures and obturators), loss of implants, loss of implant parts, loss of alveolar or supporting bone with teeth, loss of fillings (restorations including amalgams {silver}, composites {white}, porcelain or gold or metal (inlays or onlays) and any other damage to teeth, fixed or removable prostheses, surrounding and/or supporting structures not aforementioned.

It is an object of this invention to partially or completely fulfill one or more of the above-mentioned needs.

SUMMARY OF THE INVENTION

The invention comprises a dental shield device for use in intubation, comprising a plurality of segments, each segment having a male connector and a female connector located on opposite sides for attaching each segment to an adjacent segment, wherein each segment is formed from a rigid material defining a channel and a deformable material bound to an inner surface of said channel; such that a number of segments are assembleable to form the dental shield device The segment can be equally-sized, or variably-sized to fit different types of teeth. Each segment can be sized and shaped to protect one tooth or a series of teeth.

Preferably, the deformable material substantially covers all inner surfaces of said channel. Preferably, each segment is substantially trapezoidal shaped such that the channel has an outer wall longer than an inner wall, thereby allowing the dental shield device to be formed into a curve corresponding to that of a patient's teeth.

In a further embodiment of the invention, the dental shield device is provided in a kit comprising a plurality of segments assembleable into the dental shield device.

In a further embodiment of the invention, a method of preparing a patient for intubation, comprises assembling a plurality segments into a dental shield device, each segment having a male connector and a female connector located on opposite sides for the purpose of attaching each segment to an adjacent segment, and each segment formed from a rigid material defining a channel and a deformable material bound to a tooth contacting surface of said channel; and placing the assembled dental shield device over respective teeth of the patient.

In another embodiment of the invention, there is provided a dental shield device to protect the teeth of a patient during intubation, including a plurality of interconnected segments, each segment comprising a trapezoidal channel having approximately tooth-length side walls adapted to substantially enclose top, front and back portions of one tooth of the patient to protect the tooth during intubation, and having a male connector and a female connector located on opposite sides for attaching each segment to an adjacent segment, wherein a deformable material is bound to an inner surface of the channel. A spacing is provided between directly adjacent segments to provide flexibility in the dental shield device.

Other and further advantages and features of the invention will be apparent to those skilled in the art from the following detailed description thereof, taken in conjunction with the accompanying drawings.

BRIEF DESCRIPTION OF THE DRAWINGS

The invention will now be described in more detail, by way of example only, with reference to the accompanying drawings, in which like numbers refer to like elements, wherein.

DETAILED DESCRIPTION OF THE PREFERRED EMBODIMENTS

Figure 1:
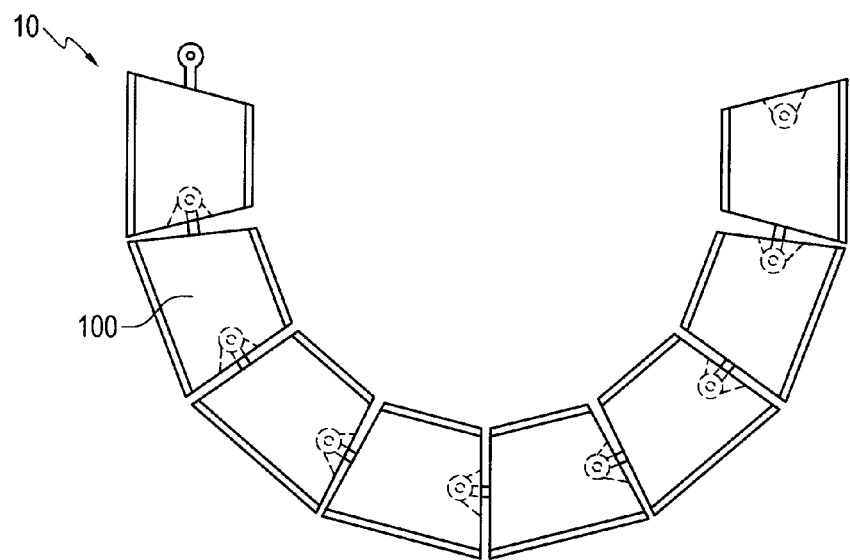
FIG. 1 is top perspective view of the assembled dental shield device according to an embodiment of the present invention.
Figure 1A:
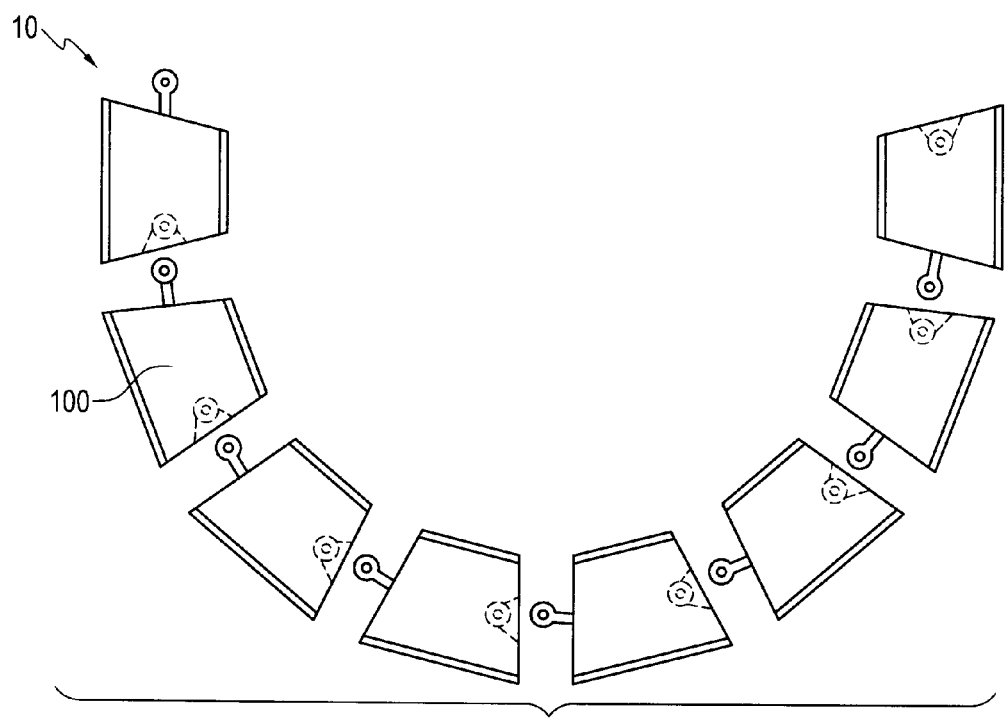
FIG. 1A is a top perspective view of the disassembled dental shield device of FIG. 1

The inventive device presented herein comprises a dental shield device 10 formed from a plurality of individual segments 100 as shown in FIG. 1 as assembled and in FIG. 1A just prior to assembly. When assembled into dental shield device 10, there is a small amount of space separating each segment 100, allowing for a degree of flexibility in the dental shield device 10.

Figure 2:
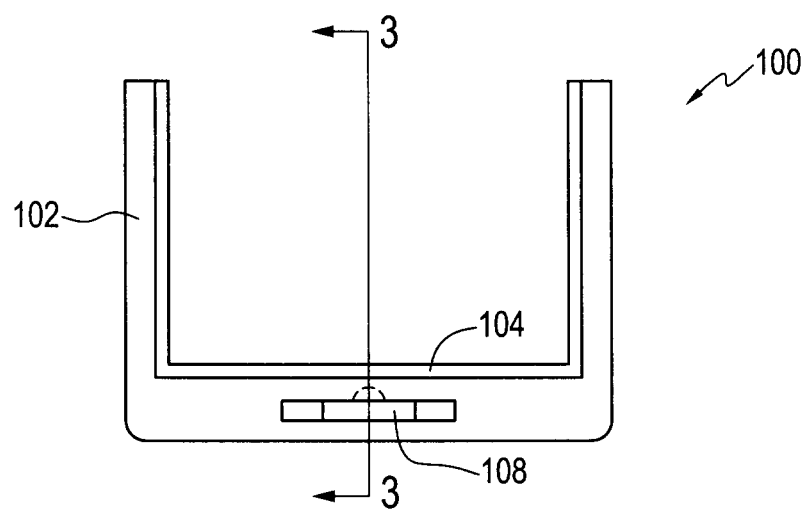
FIG. 2 is a side view of an individual segment of the device of FIG. 1.
Figure 3:
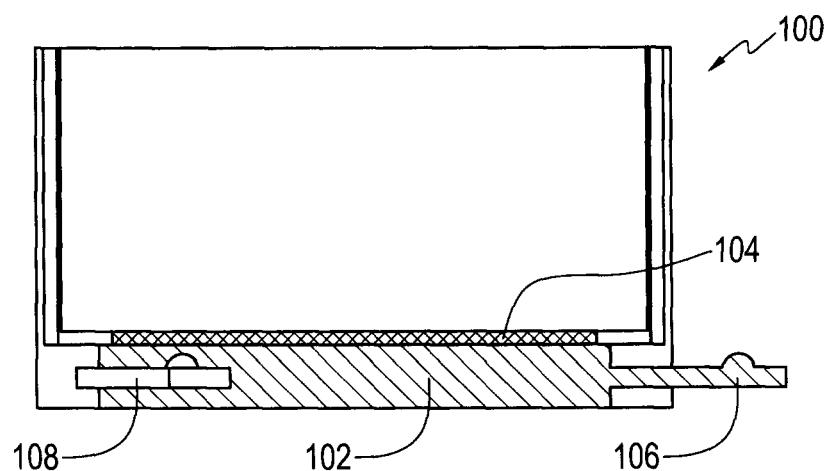
FIG. 3 is a front view of the segment of FIG. 2.
Figure 4:
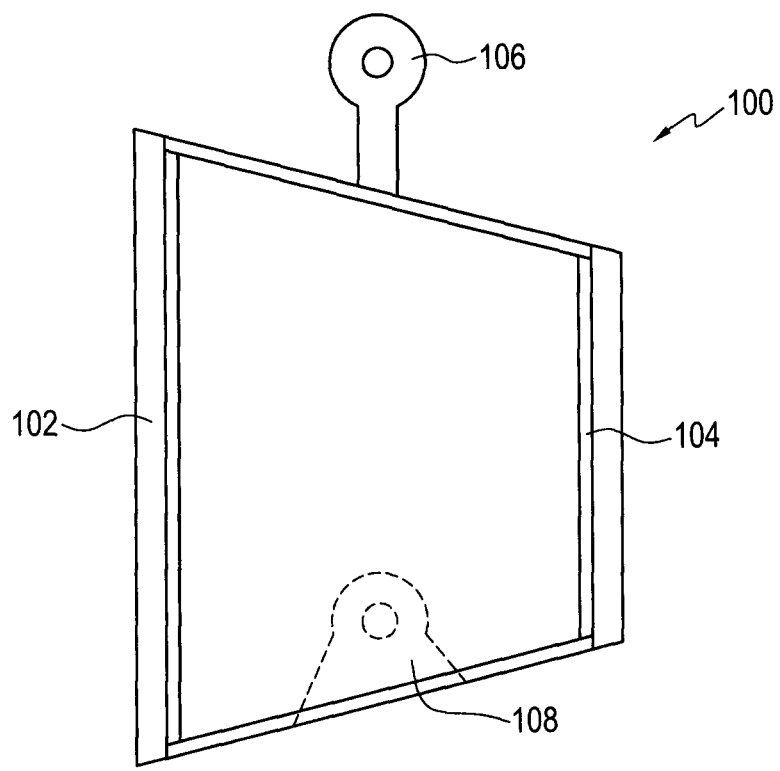
FIG. 4 is a top view of the segment of FIG. 2

The individual segments 100, as shown in FIG. 2, are formed from a tooth-sized rigid section 102 coated on the inner tooth-contacting surface with a layer of deformable material 104. Each segment 100 forms a channel which goes around the tooth and has the deformable material 104 bound to an inner surface of the channel. Each segment 100 has a male connector 106 and a female connector 108 on one end and a corresponding male connector 106 and female connector 108 on the opposite end, as shown in FIGS. 3 and 4. As shown herein, male connector 106 is a post-type connector and female connector 108 is a socket type connector, however, other suitable male/female connector types are equally acceptable for use. Preferably, the segments 100 are symmetric or near symmetric, permitting assembly in any order and orientation, as best shown in FIG. 4. The general overall shape of each segment 100 is substantially trapezoidal, permitting the segments to be assembled into an arch shaped corresponding to a human tooth pattern as shown in FIG. 1.

Figure 5:
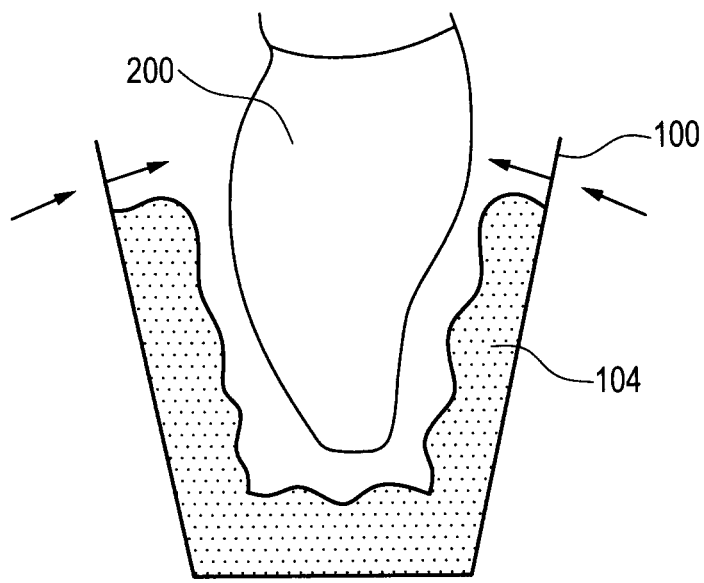
FIG. 5 is a side schematic view of a tooth prior to insertion into the segment of FIG. 2.
Figure 6:
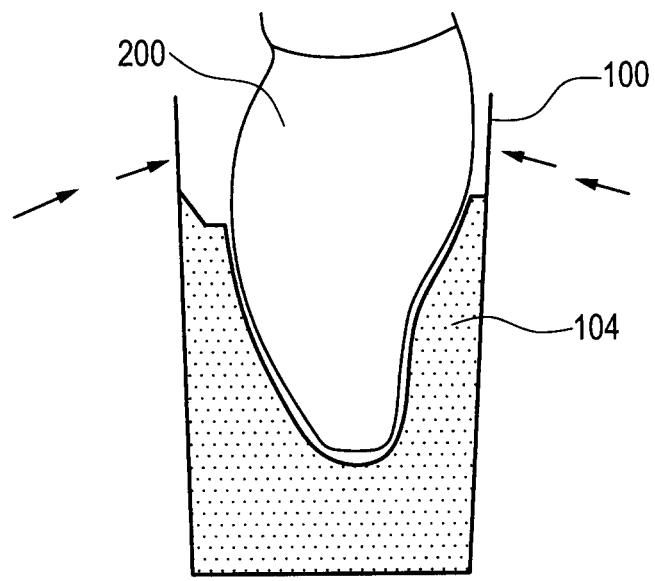
FIG. 6 is a side schematic view of a tooth after insertion into the segment of FIG. 2.

The segments 100 can be identically sized or variably-sized to reflect variations in tooth or teeth segment size and shape. Identically sized segments are more useful in emergency situations, where the dental shield 10 must be assembled rapidly. Variable-sized segments 100 are preferred for more conventional use in operating rooms as providing a superior fit to the patient's teeth. As shown in FIGS. 5 and 6, when the patient's tooth 200 is engaged with the deformable material 104, the deformable material 104 molds to the shape of the tooth 200, as best shown in FIG. 6, both securing the segment 100 to the tooth 200 and acting to dissipate pressure exerting upon the segment 100 to the entire dental shield device.

Figure 7:
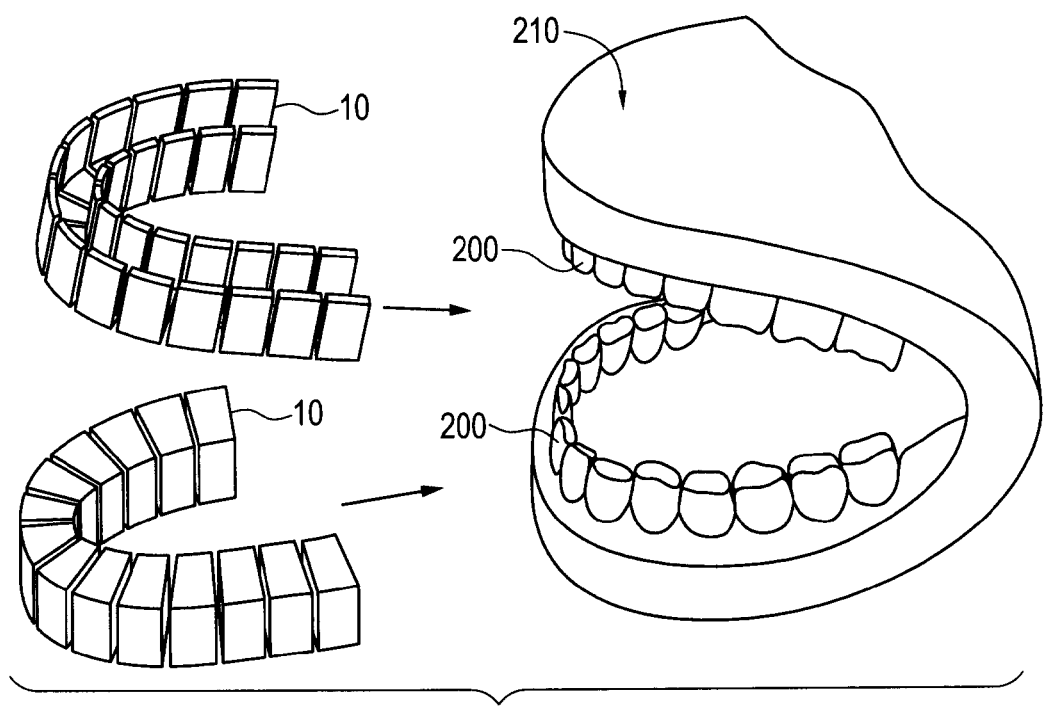
FIG. 7 is a side schematic view of a patient's mouth prior to insertion of the dental shield device of FIG. 1, with lower and upper dental shield devices of FIG. 1.
Figure 8:
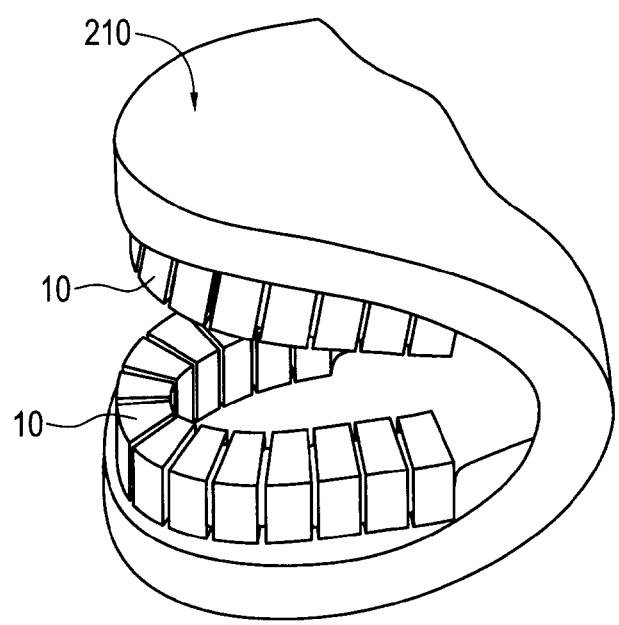
FIG. 8 is a side schematic view of a patient's mouth after insertion of lower and upper dental shield devices of FIG. 1.

In operation, the dental shield device 10 formed by assembling a plurality of segments 100 in sufficient number and of appropriate size such the dental shield device 10 is sized to cover the patient's teeth 200 as illustrated in FIGS. 7 and 8. Ideally, the dental shield device 10 capable of being assembled in a very brief amount of time, such as within 30 seconds. Once the patient's mouth 210 is opened as part of the intubation procedure, the dental shield device 10 is placed over the teeth 200, upper and/or lower, and compressed to the teeth 200 via finger pressure. The deformable material 104 contained in the segments 100 is compressed as described above and is retained in place forming suction with the teeth. As previously shown, each segment 100 of the dental shield device is separated by a small amount of space.

Once in place, the dental shield device 10 distributes any forces exerted from the intubation against the teeth 200 more equally among all the teeth on the device, preventing fracturing, chipping or other damage of the patient's teeth 200. Pressure applied by the laryngoscope blade and/or intubation tube is thus distributed over all the teeth more equally, allowing the operator to manipulate the patient's mandible to ensure a clear view for intubation as necessary to minimize the concern for damaging the patient's teeth.

This concludes the description of a presently preferred embodiment of the invention. The foregoing description has been presented for the purpose of illustration and is not intended to be exhaustive or to limit the invention to the precise form disclosed. Many modifications and variations are possible in light of the above teaching and will be apparent to those skilled in the art. It is intended the scope of the invention be limited not by this description but by the claims that follow.

What is claimed is:

1. A dental shield device to protect teeth of a patient during intubation, comprising:
    a plurality of interconnected segments, each segment comprising a trapezoidal channel having approximately tooth-length side walls adapted to substantially enclose top, front and back portions of only one tooth of the patient to protect the tooth during intubation, and having a male connector and a female connector located on opposite sides for attaching each segment to an adjacent segment, wherein a deformable material is bound to an inner surface of said trapezoidal channel; and wherein a spacing is provided between directly adjacent segments thereby providing flexibility in the dental shield device.

2. The dental shield device of claim 1, wherein said trapezoidal channel of each segment is substantially tooth-shaped such that each segment is adapted to protect one tooth.

3. The dental shield device of claim 1, wherein each of the segments is identical in size.

4. The dental shield device of claim 1, wherein the deformable material substantially covers all inner surfaces of said trapezoidal channel.

5. The dental shield device of claim 1, wherein the segments are substantially symmetrical.

6. A kit for assembling a dental shield device, comprising:
    a plurality of segments, each segment comprising a trapezoidal channel having approximately tooth-length side walls adapted to substantially enclose top, front and back portions of only one tooth of a patient to protect the tooth during intubation, and having a male connector and a female connector located on opposite sides for attaching each segment to an adjacent segment, wherein a deformable material is bound to an inner surface of said trapezoidal channel; and wherein a spacing is provided between directly adjacent segments when assembled, thereby providing flexibility in the dental shield device.

* * * * *